United States Patent
Ulbers

(10) Patent No.: US 6,644,810 B1
(45) Date of Patent: Nov. 11, 2003

(54) OPHTHALMIC APPARATUS WITH A LIGHTING AND/OR BEAM THERAPY RAY WHOSE SURFACE INTENSITY DISTRIBUTION CAN BE REGULATED AND DEVICE WITH SUCH AN APPARATUS FOR EYE TREATMENT

(75) Inventor: Gerd Ulbers, Riggisberg (CH)

(73) Assignee: Haag-Streit AG, Koniz (CH)

( * ) Notice: Subject to any disclaimer, the term of this patent is extended or adjusted under 35 U.S.C. 154(b) by 0 days.

(21) Appl. No.: 09/889,783

(22) PCT Filed: Jan. 24, 2000

(86) PCT No.: PCT/CH00/00032

§ 371 (c)(1),
(2), (4) Date: Sep. 26, 2001

(87) PCT Pub. No.: WO00/42901

PCT Pub. Date: Jul. 27, 2000

(30) Foreign Application Priority Data

Jan. 22, 1999 (CH) .................................................. 126/99

(51) Int. Cl.[7] .................................................. A61B 3/10
(52) U.S. Cl. ........................................................ 351/212
(58) Field of Search .................................. 351/200, 205, 351/206, 211, 212, 213, 214, 215, 221; 600/558

(56) References Cited

U.S. PATENT DOCUMENTS

| | | | | |
|---|---|---|---|---|
| 5,018,851 A | * | 5/1991 | Matsumura | 351/214 |
| 5,640,962 A | * | 6/1997 | Jean et al. | 600/407 |
| 5,801,807 A | * | 9/1998 | Satake et al. | 351/221 |
| 5,920,373 A | * | 7/1999 | Bille | 351/212 |
| 5,946,075 A | * | 8/1999 | Horn | 351/246 |
| 6,099,125 A | * | 8/2000 | Webb et al. | 351/211 |
| 6,206,522 B1 | * | 3/2001 | Maloney et al. | 351/205 |
| 6,299,309 B1 | * | 10/2001 | Ruiz | 351/212 |

FOREIGN PATENT DOCUMENTS

| | | | |
|---|---|---|---|
| DE | A1-4211502 | 10/1993 | |
| EP | 482340 A1 | * 4/1992 | ............ A61B/3/13 |
| EP | A1-482340 | 4/1992 | |

* cited by examiner

Primary Examiner—Marvin M. Lateef
Assistant Examiner—John R. Sanders
(74) Attorney, Agent, or Firm—Birch, Stewart, Kolasch & Birch, LLP

(57) ABSTRACT

The ophthalmological apparatus, in particular a slit lamp apparatus, has an observation unit and an illumination unit, which emits a light beam for eye observation and/or treatment purposes, the areal cross-sectional dimension of which beam can be adjusted by means of an adjustable diaphragm. The diaphragm is designed as a planar light modulator (50) which can be adjusted by a non-mechanical adjusting means and whose local optical properties can be changed and can be changed back again. A radiation impinging on the planar light modulator (50) has impressed on it by the latter a predetermined geometrical cross-sectional dimension or a predetermined areal intensity distribution as image information. This different intensity distribution has the same effect on or in the eye as the mechanical diaphragms used heretofore. A raster-free generation of image elements is achieved whenever a corresponding image is "written" or "impressed" optically e.g. with a light or laser beam or a projected imaging into the planar light modulator.

22 Claims, 3 Drawing Sheets

OPHTHALMIC APPARATUS WITH A LIGHTING AND/OR BEAM THERAPY RAY WHOSE SURFACE INTENSITY DISTRIBUTION CAN BE REGULATED AND DEVICE WITH SUCH AN APPARATUS FOR EYE TREATMENT

This application is the national phase under 35 U.S.C. § 371 of PCT International Application No. PCT/CH00/00032 which has an International filing date of Jan. 24, 2000, which designated the United States of America and was not published in English.

TECHNICAL FIELD

The invention relates to an ophthalmological apparatus, in particular a so-called slit lamp apparatus in accordance with the preamble of patent claim 1, and to an arrangement in accordance with patent claim 10.

PRIOR ART

A slit lamp apparatus as ophthalmological apparatus is known for example from Haag-Streit, under the designation "Original slit lamp 900 BM". A further slit lamp apparatus is described in the European patent application EP-A 0 916 306 (EP-98 810 895.7).

SUMMARY OF THE INVENTION

Object of the Invention

It is an object of the invention to provide an ophthalmological apparatus, in particular a so-called slit lamp apparatus, which, compared with the known apparatuses, provides the treating or examining ophthalmologist with a significantly greater area of application in one and the same apparatus with extremely simple operation. Furthermore, the intention is for this apparatus to be able to be integrated into an arrangement for eye treatment.

How the Object is Achieved

The way in which the object is achieved is the subject matter of patent claim 1.

Specifically, compared with the known apparatuses, the invention no longer has a mechanical diaphragm by means of which the geometrical cross-sectional form of an examining light beam can be adjusted. According to the invention, then, the cross-sectional intensity distribution of a light stria (slit) required for the eye examination is performed by means of a so-called planar light modulator. The adjustable optical properties of this planar light modulator are adjusted or altered in a simple manner at predeterminable and freely selectable locations by means of the procedures presented below. The optical properties over the irradiatable region of the planar light modulator can then be altered—under remote control—in such a way that a desired optical structure with predeterminable optical properties is achieved. This optical structure then alters a light beam incident on it either in transmission or reflection in accordance with the required intensity distribution. This different intensity distribution generally has the same effect on or in the eye— except for differences presented below—as the mechanical diaphragms used heretofore. The geometrical cross section of an illumination beam can now be rapidly altered in a simple manner. However, it is likewise possible to generate from it in a simple manner a light band, an arrangement of lines, an arrangement of points or some other optical figures for the eye illumination or examination, i.e. to change its intensity distribution.

Depending on the planar light modulator (described below) used, it is possible to generate intensity distributions, i.e. images, whose individual image elements have a raster or are raster-free, a raster, analogously to general printing technology, being understood as an arrangement of equidistant points. The arrangement of spaced-apart points may, of course, be different; but it is always identical in one and the same image. A raster is obtained whenever image elements in a planar light modulator are activated by matrix-like, in general electrical driving. However, in this case a raster is not understood as an arrangement of points as is used below for determining imaging errors of the eye.

With a planar light modulator operating in a raster-free manner, in contrast to a planar light modulator operating with a raster, it is possible to generate e.g. areal image elements with a constant optical property without internal structure.

A raster-free generation of image elements is achieved e.g. when a corresponding image is "written" or "impressed" optically with a light or laser beam or a projected imaging into the planar light modulator. In this case, depending on their intensity distribution over the beam cross section, the "writing beams" can be moved in a manner overlapping one another in the beam edge region in such a way that an image element with constant luminance can be generated by the area region respectively written to. It goes without saying that variable luminances can also be generated. In addition to the optical figures in a bright/dark representation mentioned below, it is also possible to generate figures with different gray tones.

A differentiation in use between these two types of planar light modulators is important since different perceptions can be generated in the eye by this means and different test methods can thus also be performed on the eye. Specifically, for an observer to be examined, a completely different impression is given in the case of intrinsically rastered optical figures and figures with a raster-free intensity profile.

Hitherto, in the case of the slit lamp apparatuses known for examinations, the person skilled in the art of ophthalmology had always proceeded from an adjustable mechanical diaphragm. It was obvious to use such a diaphragm since the intention was in each case to image a light band with a surrounding dark region on the eye or within it, and this was generated precisely by means of a mechanical diaphragm, as e.g. also in the case of cameras. If, in a departure from a simple light band, for keratometric measurements, the intention was to image geometrical structures on or in the eye, then in this case, to, as described in U.S. Pat. No. 5,418,582, mechanical diaphragms with completely translucent and completely blocking diaphragm regions were used. By means of the invention described below, in a simple manner, without any change in hardware, it is possible for example also to image the geometrical structure generated with the ring cone of U.S. Pat. No. 5,418,582, in addition to a customary light band imaging.

By means of a planar light modulator of this type, it is possible, then, to generate a "light band" having dimensions and an intensity distribution as corresponds to the conventional one, which was performed by means of a mechanically adjustable diaphragm. Over and above such a "light band", it is now possible, however, to generate any desired intensity distributions and figures. It is now possible to generate e.g. a multiplicity of light bands which are parallel to one another or are at any desired angles with respect to one another. Moreover, it is possible to generate annuli, full circles, Placido rings, cross gratings, . . .

Since image information for a video recording unit can be extracted from the observation beam path, as described, in particular, in EP-A 0 916 306 (EP-98 810 895.7) already mentioned, automatic evaluation can, moreover, be performed. The original image can be compared with its projection on curved areas such as the cornea and retina. From this comparison, the corresponding curvatures can then be determined automatically by an evaluation unit.

The apparatus according to the invention is thus excellently suitable, in addition to the examinations and treatment methods of a slit lamp apparatus already known, for cornea thickness measurement, for creation of a 2D or 3D fundus profile, for cornea topography, for fundus topography,

BRIEF DESCRIPTION OF THE DRAWINGS

Examples of the apparatus according to the invention are explained in more detail below with reference to the drawings, in which.

WAYS OF EMBODYING THE INVENTION

Figure 1:
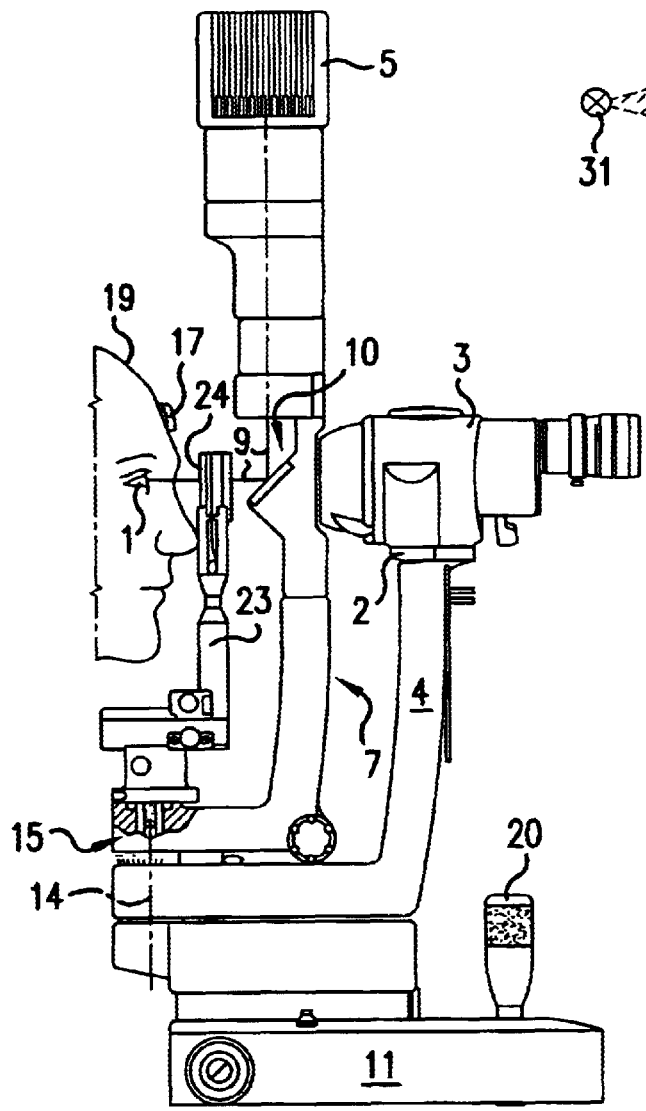
FIG. 1 shows a side view of an ophthalmological apparatus according to the invention as slit lamp apparatus, the exterior of which differs only slightly from that of an already known slit lamp apparatus; a video recording unit which can be flanged onto the observation unit is not used here; the flanging-on location is closed off by a stopper 2.

The ophthalmological apparatus illustrated in FIG. 1 is designed as so-called slit lamp apparatus and serves for stereoscopic observation of a human eye 1. The slit lamp apparatus has an observation unit 3 and an illumination unit 5. The observation unit 3 is held by means of an L-shaped holding unit 4 and the illumination unit 5 is held by means of a further L-shaped holding unit 7. The illumination unit 5 emits a light beam 9 which can be guided via a deflection mirror 10, which is arranged on the holding unit 7, into or onto the eye 1. The intensity distribution of the light beam 9 over its cross section is adjusted by means of a planar light modulator, whose method of operation is described below. The holding unit 7 is arranged on an apparatus base 11 in a manner that it allows to pivot via a pivoting articulated joint 15 with a vertical pivot axis 14. The position of the axis 14 is chosen such that it runs past a human forehead 19 at the front side of the eye, said forehead being placed against a forehead strip 17 (only indicated in the drawing) of a head holder (not illustrated).

The observation unit 3 may be designed as a Greenough microscope out of whose beam path image information could be diverted into a video recording unit (not illustrated), as is described in detail, in particular, in EP-A 0 916 306 (EP-98 810 895.7) cited above. Consequently, besides visual observation, it is additionally possible to perform video recordings with a video unit 22 for direct observation, for recording (documentation) or automatic evaluation.

Between the deflection mirror 10 and the human eye to be examined or to be treated, there is arranged here, for example, for the observation of the fundus of the eye, an imaging lens 21 on a lens holder 23 with an additional lens 24, which lens holder can be fitted into the pivoting articulated joint 15. The fundus of the eye can be observed using this arrangement. The configuration of said lens holder 23 is likewise described in detail in EP-A 0 916 306 (EP-98 810 895.7). If the cornea of the eye is observed, the additional lens 24 with its lens holder 23 is pivoted away. The positioning of the apparatus horizontally in the X- and Y-direction is performed with the aid of a steering lever 20, often also referred to as "joystick", arranged on the apparatus base 11.

Figure 2:
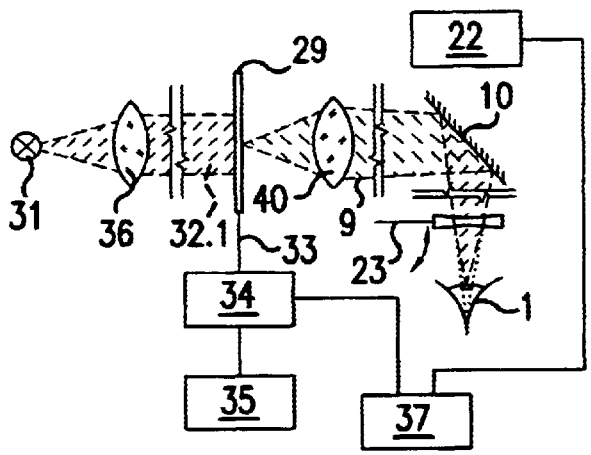
FIG. 2 shows a block diagram of an exemplary embodiment of an illumination unit of the apparatus illustrated in FIG. 1, a planar light modulator being operated in transmission.

FIG. 2 shows a block diagram of an exemplary embodiment of an illumination unit 5 for observation of the fundus of the eye. In this exemplary embodiment, a planar light modulator 29 is used as adjusting means for the intensity distribution of a light beam 9—emitted by a light source 31—over its cross section. The terms light beam and light source are understood somewhat more broadly here by not necessarily being geared to visible light. Light source 31 is in this case also understood to include laser light sources. The planar light modulator 29, whose configuration is explained below, is used in transmission here. The planar light modulator 29 is connected to a drive electronic unit 34 via electrical signal lines 33. Depending on signals on the drive lines 33, different microstructure regions on the planar light modulator are driven in such a way that their local transmission distribution for the radiation of the light source 31 changes. In signal terms, the drive electronic unit 34 is connected to an input unit 35 and to an evaluation electronic unit 37, which is in turn connected to the video unit 22 in signal terms. The driven microstructure regions of the planar light modulator 29 are uniformly illuminated by a light beam 32.1 emitted by the light source 31, which light beam is formed into a collimated beam for example by a collimator lens 36. The desired transmission distribution in the areal modulator 29 is then achieved depending on the selected driving of the relevant microstructure regions by the drive electronic unit 34. The radiation which emerges from the planar light modulator 29 and contains the image information of the driven modulator 29 is focused by an imaging system 40 onto the cornea of the eye, or is focused with interposition, as illustrated in FIG. 2, onto the fundus of the eye using the additional lens 24. The imaging is then observed using the observation unit 3 or evaluated by means of the signals of the video unit with the evaluation electronic unit 37.

Figure 3:
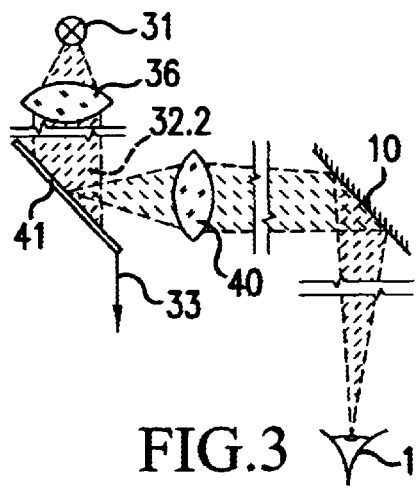
FIG. 3 shows a block diagram with a variant with regard to the illustration in FIG. 2, the planar light modulator in this case being operated in reflection; the additional lens which can be pivoted in and out with a pivotable lens holder as in FIG. 2 is no longer illustrated here.

Instead of operating the planar light modulator 29 in transmission, as shown in FIG. 2, a differently constructed planar light modulator 41 can also be operated in reflection, as indicated in FIG. 3.

In addition to electrical planiform driving, it is also possible to impress (write) an image information item on a planar light modulator with an auxiliary radiation. The wavelength of the writing radiation then differs from the radiation with which the written-in image information is read out, i.e. imaged onto or into the eye. When using this auxiliary radiation, it is possible to work in transmission or in reflection depending on the construction of the planar light modulator.

Figure 4:
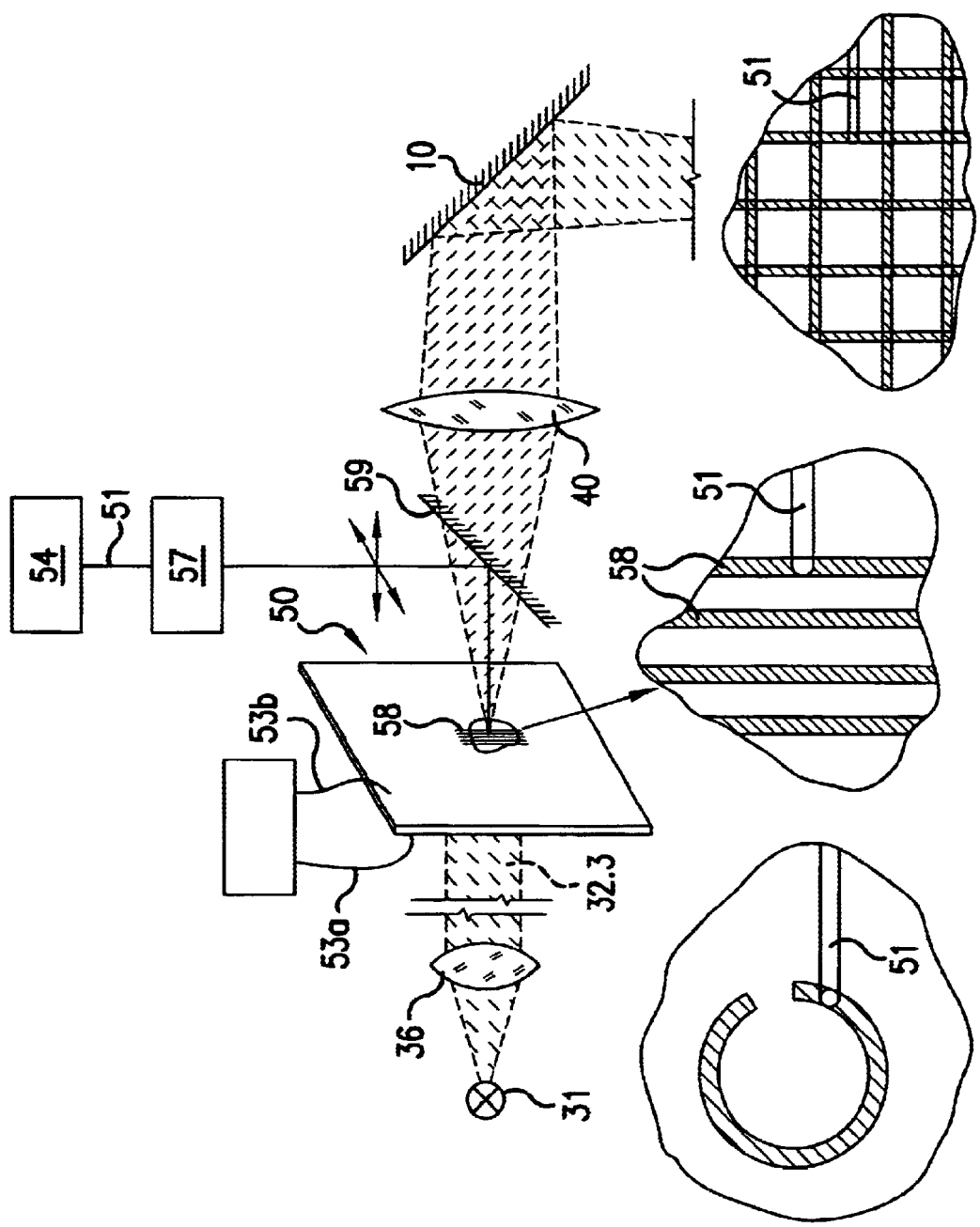
FIG. 4 shows a variant with regard to the illustration in FIG. 2, in this case a raster-free "diaphragm information item" being written with a light or laser beam.

FIG. 4 shows a planar light modulator 50, which is operated in transmission and in which an image information item can be written by means of a laser beam 51. A liquid crystal (nematic phase) with solids distributed in it, as described in DE-A 42 11 502, can be used as the planar light modulator 50. In this case, since operation takes place in transmission, the liquid crystal is arranged between two transparent plates, preferably made of glass, on which likewise transparent electrodes 53a and 53b are vapor-deposited. Liquid crystals that can be used and the solids to be incorporated in them and production methods in this respect are described in DE-A 42 11 502. To locally change optical properties in the planar light modulator 50, the latter can be swept over by a laser beam 51, which can be emitted by a laser source 54. The laser beam 51 can be areally deflected by a beam deflection unit 57. The intensity of the laser beam 51 can be switched on and off by way of the excitation of the laser source, by means of a (not illustrated) resonator-internal or -external switch, or the intensity thereof can be adjusted. The planar light modulator 50 operates in a raster-free manner.

Before an image information item is written, it is preferable firstly to perform a homeotropic molecular orientation of the molecules of the liquid crystal. This orientation can be effected e.g. by an AC voltage at, for example, 500 Hz with 100 $V_{rms}$ being applied to the electrodes 53a and 53b, in accordance with DE-A 42 11 502. However, the same orientation can be achieved at a lower voltage in the case of simultaneous irradiation with the radiation of a semiconductor laser. An image information item is then written in the case of deenergized electrodes 53a and 53b with a higher laser power. The written-in image elements are then distinguished from those not written in by virtue of a pronounced light-scattering effect.

If the laser beam 51 is then deflected by the beam deflection unit 57 in such a way that a row of lines are "written" in a manner overlapping at the line edges, then it is possible, in accordance with the number of lines and their length, to write a band 58 having predetermined width and length (height) [in accordance with the action of a mechanically adjustable diaphragm] with a predetermined luminance to be generated or with a luminance that has a predetermined profile but is raster-free. After the "writing-in process", the planar light modulator 50 is illuminated with a radiation 32.3 analogously to the optical construction of FIG. 2. An imaging of the planar light modulator 50 with the imaging system 40 then produces an imaging of a light band on the cornea or the retina, depending on whether the lens 24 is used. The width and length of the light band can then be completely erased by erasing the written-in image information in the liquid crystal, as described above, and be written in anew again with other geometrical dimensions.

However, it is also possible to perform only a partial erasure of an image information item that has already been written in, if a lower AC voltage is applied to the electrodes and the region to be erased is swept over by the laser beam. Voltage values and intensity values for the laser beam or exposure times depend on the wavelength of the laser and the liquid crystal material used. A selection of data can be gathered from DE-A 42 11 502.

Small mirrors or one or two acousto-optical deflectors can be used as beam deflection unit 57. For writing in an image information item or for partly erasing it, the laser beam can be directed at the surface of the planar light modulator which faces the light source, or, as illustrated in FIG. 4, from the other, opposite side. If radiation is radiated onto the opposite side, then the laser beam must either be directed obliquely at this surface, to ensure that it does not then disturb the imaging later on, or be radiated via a coated mirror 59, which reflects the radiation from the laser but transmits the radiation from the light source 31, onto the opposite side of the planar light modulator (see FIG. 4). The arrangement mentioned last has the advantage that the writing laser radiation can never enter the eye to be examined.

DE-A 20 32 212 describes a further planar light modulator which can be used analogously to that in DE 42 11 502. In this case, too, a liquid crystal is used with whose material a dichromatic substance is admixed (e.g. p-n butoxybenzoic acid as nematic liquid crystal and methyl red as dichromatic dye). This planar light modulator is a plate with a sandwich-like construction. A transparent areal electrode is respectively arranged on the outer sides. If, in contrast to the embodiment in DE-A 20 32 212, one of the areal electrodes is now designed in such a way that electrical driving of partial electrodes arranged at predetermined locations is possible, the intervening molecules can then be oriented only between these respectively driven partial electrodes and the opposite extended electrode, as a result of which the transmission of this microstructure region is increased relative to the "non-driven" ones.

Instead of writing optical information to a liquid crystal in particular optically and thus in a raster-free manner, it is also possible to write to an electro-optical ceramic of a planar light modulator. Materials that can be used for this purpose are described in DE-A 24 16 684. Fast writing and also erasure of an image information item is possible. The electro-optical ceramic material of the planar light modulator, in which there may be a ferroelectric phase and an antiferroelectric phase or paraelectric phase beside one another with a morphotropic phase, may be solid solutions of the general formula

The parameters x, α, y, β, A and M presented in the formula should be selected in accordance with the details below:

$0 \leq x \leq 0.2$;

$0 \leq \alpha < 1$;

$0 \leq y \leq 0.6$;

$0 < \beta < 1$, $0 < (y+\beta) \leq 1$,

A denotes at least one element from the group of divalent and trivalent alkaline earth and rare earth elements;

M denotes at least one element from the group of tetravalent and pentavalent metals.

The electro-optical crystal has a thickness of about 200 μm. Electrically conductive, optically transparent electrodes (e.g. made of $SnCl_4$) 63a and 63b are applied on its front and rear sides. If the intention is only to generate already previously known images, then the electrodes can be applied with the corresponding geometrical dimensions of the images to be generated. If the intention is to achieve the possibility of great variation of images, then a multiplicity of individually drivable partial electrodes are applied. One electrode 63a of the two electrodes 63a and 63b extends over the entire surface of the field 64 provided for writing information. The electrode arrangement e.g. 63b located on the other side then has the desired structuring. In order to write an image, for example in the case of $Pb_{0.914}La_{0.084}A_\alpha$ $(Zr_{0.65}Ti_{0.35})_{0.979}O_3$, a voltage of 80 V is applied to selected partial electrodes of the electrode arrangement 63b between it and the areal electrode 63a. Under these driven partial electrodes, a ferroelectric phase is then produced in the electro-optical crystal; a region is produced which causes rotation of the plane of polarization (birefringence) of light incident on said region, or scattering of said light. In regions which remain in the antiferroelectric phase or the paraelectric phase, radiated light is not subjected to scattering or birefringence. This property of the driven regions is also maintained after the voltage has been switched off, provided that a typical stability temperature Th is not exceeded for the relevant material of the liquid crystal. Depending on the material used, this temperature Th lies between 25° C. and 70° C. A material selection in this respect is specified by DE-A 24 16 684.

Figure 5:
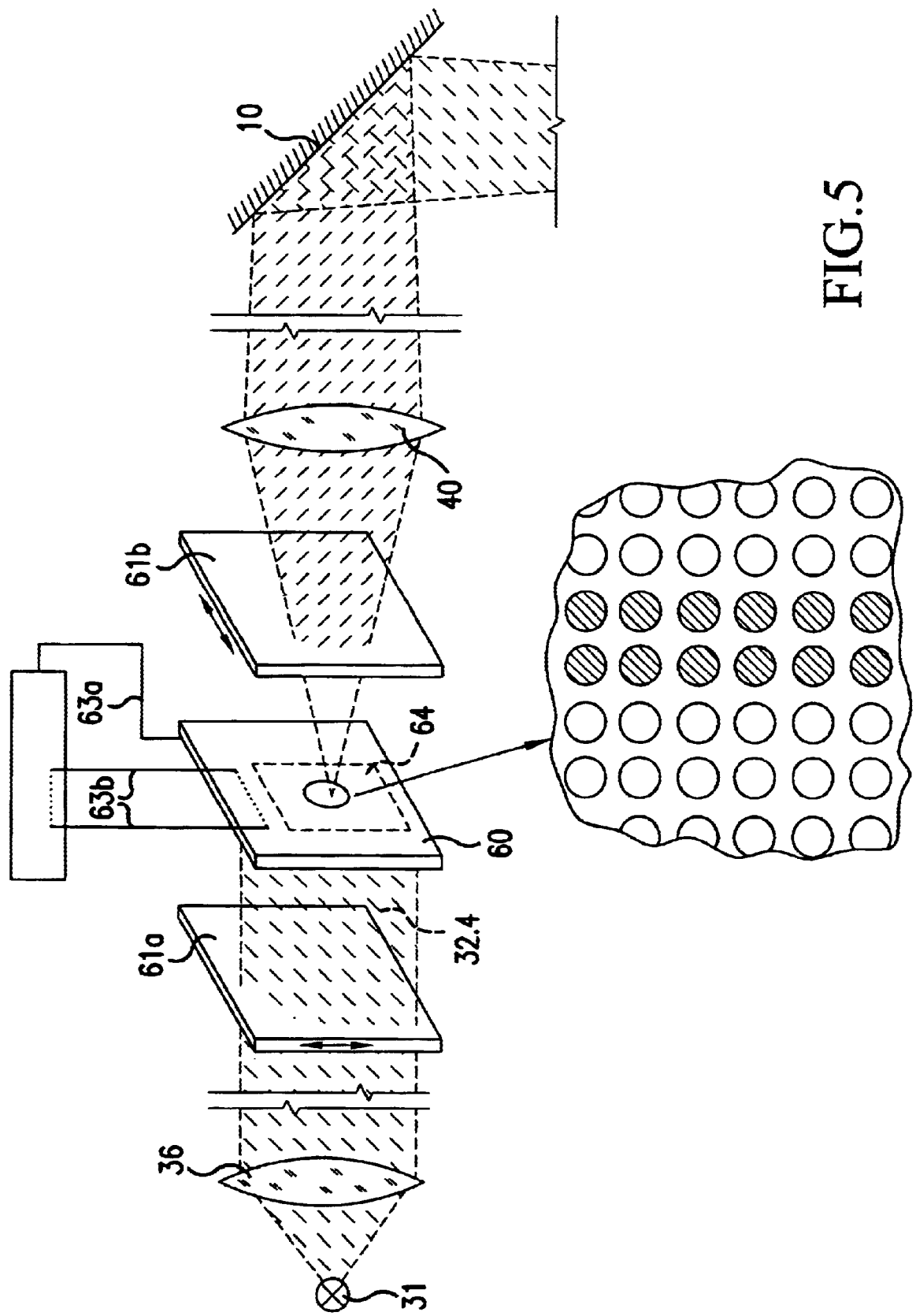
FIG. 5 shows a further variant in which the direction of polarization of transmitted radiation can be locally rotated by means of the planar light modulator.

If a planar light modulator 60 designed in this way is situated between two polarizers 61a and 61b (polarizer 61a, analyzer 61b) whose directions of polarization are crossed, as is indicated in FIG. 5, then only the driven microstructure regions are imaged by the optical imaging system 62 on the cornea of the eye or the retina, depending on whether the additional lens 24 is used.

In addition to the electrode arrangements 63a and 63b required for writing or impressing an image information item, electrodes are arranged outside the field 64, by means of which electrodes a current flow, preferably a pulsating current flow, can be impressed and leads to crystal heating which is distinctly in excess of the abovementioned stability temperature Th. The "erasure electrode arrangement" is to be chosen such that in the information field 64 an external electric field prevails with a polarity which is opposite to the "written-in polarization", while the field 64 is simultaneously heated.

The electrode arrangement 63a can then be replaced by a photoconductor layer and be "written to" by a light beam or a laser beam in accordance with the above explanation with respect to FIG. 4. Such an impressed information item can then likewise be imaged onto the cornea of the eye or the fundus of the eye.

However, it is also possible to embody a planar light modulator 41 using an image reproduction apparatus described in DE-C 20 11 575. In addition to the arrangement with a nematic liquid crystal as already described in DE-A 24 16 684, a schlieren optical imaging is demonstrated here. With a comb-like electrode arrangement, on a medium whose thickness can be deformed (e.g. a polarized silicone oil layer adhering on a surface) is deformed in a wave-like manner. This layer deformed in a wave-like manner is irradiated from "behind" by a projection light pencil—having a strip-like structure—at an angle such that total reflection occurs. The totally reflected projection light pencil with its strip structure, on which a wave structure is superposed, impinges on a strip-like diaphragm whose strips are arranged in such a way that no light of the projection pencil can pass through. A photoconductor is arranged at a short distance from this deformable layer. If said photoconductor is exposed, then a charge distribution corresponding to the exposure is produced on it, which charge distribution then additionally deforms the deformable layer, as a result of which, in a manner corresponding to the deformation, projection light passes through the strip-like diaphragm in a manner corresponding to the image information (=schlieren optical imaging). In a further development of DE-C 20 11 575, however, the photoconductor can be replaced by a vapor-deposited, electrically conductive grating whose grating points are then correspondingly driven by the drive electronic unit in order to generate the required charge pattern with the desired image information. The optical arrangement to be used then corresponds to that shown in FIG. 3. Raster-free images can be generated with this planar light modulator as well.

In reflection, it is possible to use the planar light modulator of DE-A 196 24 276. The planar light modulator described in this case operates with a phase modulation of light reflected from a mirror. By virtue of this phase modulation, the desired image information, as is required in the above-described ophthalmological apparatus for the eye examination, is impressed on the light. A plurality of dielectric solid layers together with a deformable plastic dielectric top layer act as mirror. Said top layer may be a dielectric liquid, for example a silicone oil. The dielectric liquid is then situated within an electrode raster arrangement, whose raster corresponds to the selected microstructure regions. If one of the raster points is then electrically driven, this produces an alteration of the thickness of the plastic dielectric layer, which means that the phase relationship for total light mirroring is then no longer provided. This image point can thus be imaged.

The size of the regions to be produced with predetermined optical properties of the planar light modulator and the density thereof depend on the imaging conditions and the desired geometrical resolution. For a function of an above-indicated "diaphragm simulation" or generation of a predetermined geometrical pattern on the eye, the retina or other curved areas, it is possible, in accordance with the above explanations, to use a planar light modulator whose image regions operate either in reflection or in transmission for the imaging radiation (light).

If reflection is worked with, then it is possible to change the reflection factor, the transmission factor and also the phase delay time upstream of a rear mirror or the reflection direction (schlieren optical arrangement). If the design is geared to transmission, then it is likewise possible to work with the schlieren optical method and also to undertake a different absorption, a different phase delay time, and also a different angle of rotation of the polarization of the transmitting light.

The driving in the case of existing microstructure regions can be implemented electrically, which generally leads to a luminance raster of the image elements. However, it is also possible to implement an optical imaging (e.g. light/laser beam or projected image) on the surface of the planar light modulator, in which case the planar light modulator then acts as a light amplifier and a raster-free and thus also a structure-free (in the image element) luminance can be generated in this case.

It would also be possible to produce a "diaphragm configuration" to be amplified with an LCD display, which is then amplified with the planar light modulator and correspondingly imaged with an optical system.

The diaphragm effect of the planar light modulator has been described above only with regard to observation and measurement purposes. However, such a planar light modulator can also be used for beam shaping of a light or laser beam for treatment on the eye.

Instead of using the above-described planar light modulator for illuminating the cornea of the eye or the fundus of the eye, it can also be used as an adjustable diaphragm for a treating light or laser beam.

Using the above-described ophthalmological apparatuses outlined in FIGS. 2 to 5, glaucoma patients can also be successfully examined in addition to a series of applications. By way of example, using the planar light modulators described above, it is possible to generate ring structures which are then illuminated by light sources of different colors. It is possible to generate e.g. a blue luminous ring which is imaged onto the retina of the eye. The patient is then asked what he discerns and where the ring is interrupted. The local position of retina damage can then be inferred from the position of absent (interrupted) ring segments. An analogous measurement will subsequently be carried out using a white or differently colored ring. This is because damage to regions on the retina is not the same for all color perceptions of the patient. It goes without saying that, in the course of this examination, it is also possible to adjust and alter the luminance on the retina. A blue ring, i.e. a short-wave radiation, is used because blue sensitivity is the first to be reduced in the case of incipient retina damage.

Using the apparatuses described above, imaging errors of the eye can also be determined and automatically measured. Using the planar light modulator, a pattern of dots is generated and the position thereof on the retina is determined by measuring reflected-back radiation. This measurement is preferably carried out using infrared radiation, that is to say radiation invisible to the patient, in a darkened room. This is because the pupil is completely open in this case, which means that errors, caused by the eye lens, can readily be determined.

The evaluation will preferably be performed using a digital video camera coupled, for example, into the beam path of an observation microscope. The measurement data and also the automatically determined results can be stored and passed on to processing apparatuses. It is thus possible to determine imaging errors which are passed on to an apparatus for eye lens ablation.

If different wavelengths, preferably at least three different wavelengths, are used for measurement, it is possible to determine the chromatic aberration of the eye.

It is thus possible to perform a corresponding treatment immediately after the measurement. Moreover, measurement can be continually carried out during the treatment.

What is claimed is:

1. An Ophthalmological apparatus comprising,
   an observation unit;
   an illuminating unit,
   from which an illumination beam emission is emittable in order to observe the eye,
   said illumination beam emission having a planar geometrical cross-sectional dimension and a two-dimensional intensity distribution; and
   a spatial light modulator having spatial optical properties, but no mechanical adjustment means,
   the spatial optical properties of said spatial light modulator are alterable and again reversible in order to confer said planar geometric cross-sectional dimension to a predetermined geometric cross-sectional dimension or said two-dimensional intensity distribution to a predeterminable two-dimensional intensity distribution in the form of an image information, on the beam emission incident upon the spatial light modulator, wherein
      a second beam emission differs from the illumination beam emission,
      the optical properties of the spatial light modulator are alterable by irradiation with said second beam emission,
      so that the image information generated with the spatial light modulator has raster-free image subareas.

2. The Apparatus according to claim 1, wherein
   the optical properties on or in the spatial light modulator are arranged to be generated and/or altered remotely by at least one electrical signal.

3. The Apparatus according to claim 1, wherein
   the optical properties on or in the spatial light modulator are arranged to be generated and/or altered remotely in adjustable local distributions by at least one electrical signal.

4. The Apparatus according to claim 1, wherein
   the alterable optical properties are locally predeterminable phase delays or phase angle rotations for the illumination beam emission of the spatial light modulator.

5. The Apparatus according to claim 1, wherein
   the alterable optical properties are reflection factors or reflection directions for the illumination beam emission that are locally predeterminable over the area of the spatial light modulator.

6. The Apparatus according to claim 1, wherein
   the alterable optical properties are scattering factors for the illumination beam emission that are locally predeterminable over the area of the spatial light modulator.

7. The Apparatus according to claim 1, wherein
   the spatial optical properties of the spatial light modulator are adjustable such that, as a two-dimensional intensity distribution, a slit adjustable in slit width and/or height is produced, the slit image of which and/or the region surrounding it are/is of raster-free structure.

8. The Apparatus according to claim 1, wherein
   said illumination unit has an optical unit,
   the spatial optical properties of the spatial light modulator are adjustable such that, as a two-dimensional intensity distribution, a geometric figure is produced,
   wherein the geometric figure is mappable using said optical unit onto the eye and/or onto the fundus of the eye.

9. The Apparatus according to claim 8 form evaluating the convexity of the cornea or the fundus of the eye.

10. The Apparatus according to claim 8, wherein
    the geometric figure has image elements arranged in a reticulated manner,
    which are useable for determining the topography of the front surface of the eye.

11. The Apparatus according to claim 8, wherein the geometric figure comprises as image element at least one first ring,
    wherein each first ring is producible at any location of the spatial light modulator,
    and each first ring can be irradiated with at least one predeterminable wavelength of an illumination beam emission in order to map on the retina of the eye at least a second ring.

12. The Apparatus according to claim 11 wherein the apparatus is used to determine local retina damage.

13. The Apparatus according to claim 8, wherein
    the geometric figure comprises as image element at least one first ring,
    wherein each first ring is producible at any location of the spatial light modulator,
    and each first ring can be irradiated with several predeterminable wavelengths of an illumination beam emission in order to map on the retina of the eye several colored second rings.

14. The Apparatus according to claim 8, wherein
    the geometric figure comprises as image element at least one first ring,
    wherein each first ring is producible at any location of the spatial light modulator, and each first ring can be irradiated with several predeterminable wavelengths of an illumination beam emission in order to map on the retina of the eye several colored second rings in succession.

15. The Apparatus according to claim 1, wherein the apparatus is designed as a slip lamp apparatus.

16. An Arrangement having an eye treatment device comprising, an ophthalmological apparatus having
 an observation unit;
 an illuminating unit,
  from which a illumination beam emission is emittable in order to observe the eye,
   said illumination beam emission having a planar geometric cross-sectional dimension and a two-dimensional intensity distribution;
a spatial light modulator having spatial optical properties, but no mechanical adjustment means,
a second beam emission differing from the illumination beam emission,
 the spatial optical properties of said spatial light modulator are alterable by irradiation with said second beam emission and again reversible,
 in order to confer said planar geometric cross-sectional dimension to a predetermined geometric cross-sectional dimension or said two-dimensional intensity distribution to a predeterminable two-dimensional intensity distribution in the form of a geometric figure with raster-free image portions,
  wherein said geometric figure is mappable using an optical unit of the illuminating optics onto the eye and/or onto the fundus of the eye, in order to evaluate the convexity of the cornea or the fundus of the eye,
  the geometric figure comprises image elements arranged in the manner of a net,
   which are useable for determining the topography of the front surface of the eye; and
a data processing unit,
 wherein the observation unit has an image-recognition unit
  with which the geometric figure mapped on the retina is recognizable and analyzable,
  the analyzed data is transferable to the data processing unit and this controls the treatment device for treatment of the eye.

17. The Arrangement according to claim 16, wherein the geometric figure comprises as image element at least one first ring, wherein each first ring is producible at any location of the spatial light modulator, and each first ring can be irradiated with at least one predeterminable wavelength of an illumination beam emission in order to map at least one colored second ring on the retina of the eye.

18. The Arrangement according to claim 16, wherein the arrangement is used to determine local retina damage.

19. The Arrangement according to claim 16, wherein the geometric figure comprises as image element at last one first ring, wherein each first ring is producible at any location of the spatial light modulator, and each first ring can be irradiated with several predeterminable wavelength of an illumination beam emission in order to map on the retina of the eye a plurality of different colored second rings.

20. The Arrangement according to claim 16, wherein the geometric figure comprises as image element at least one first ring, wherein each first ring is producible at any location of the spatial light modulator, and each first ring can be irradiated with several predeterminable wavelength of an illumination beam emission in order to map on the retina of the eye a plurality of different colored second rings one after the other.

21. The Arrangement according to claim 16, wherein the arrangement is a laser therapy device.

22. The Arrangement according to claim 16 wherein the ophthalmological apparatus is a slit lamp apparatus.

* * * * *